United States Patent [19]

Doty

[11] Patent Number: 4,952,146

[45] Date of Patent: Aug. 28, 1990

[54] DENTAL CONTROL UNIT

[76] Inventor: Susan Doty, 7501 Deerhill Dr., Clarkston, Mich. 48016

[21] Appl. No.: 317,758

[22] Filed: Mar. 2, 1989

[51] Int. Cl.$^5$ ............................................. A61G 1/14
[52] U.S. Cl. ....................................... 433/77; 312/209
[58] Field of Search ....................... 433/29, 77, 79, 98; 312/209

[56] References Cited

U.S. PATENT DOCUMENTS

| | | |
|---|---|---|
| 1,257,936 | 2/1918 | Russell . |
| 2,308,812 | 1/1943 | Jankelson ............................... 433/77 |
| 3,271,860 | 9/1966 | Burton .................................. 433/27 |
| 3,280,458 | 10/1966 | Deeley et al. . |
| 3,584,927 | 6/1971 | Ott et al. . |
| 3,597,033 | 8/1971 | Sloura . |
| 3,817,588 | 6/1974 | Helmers . |
| 4,359,316 | 11/1982 | Kummel et al. ....................... 433/79 |

Primary Examiner—John Weiss
Assistant Examiner—Michael Lynch
Attorney, Agent, or Firm—Gifford, Groh, Sprinkle, Patmore & Anderson

[57] ABSTRACT

This patent discloses a dental control unit, such as a dental cart, having a housing with four side walls, a lid pivotally secured to one side wall and movable between an open position and a closed position. A plurality of knobs, gauges, buttons, etc. are provided along one side wall. A transparent shield is secured to the lid so that, with the lid in its closed position, the transparent shield overlies and covers the various control members. Conversely, the control members are accessible once the lid is opened. The lid provides an outer smooth surface which facilitates the cleaning and disinfecting of the dental cart after patient use. The shield can also be used with other dental control units, such as a front delivery system and a rear delivery system.

7 Claims, 1 Drawing Sheet

U.S. Patent      Aug. 28, 1990      4,952,146
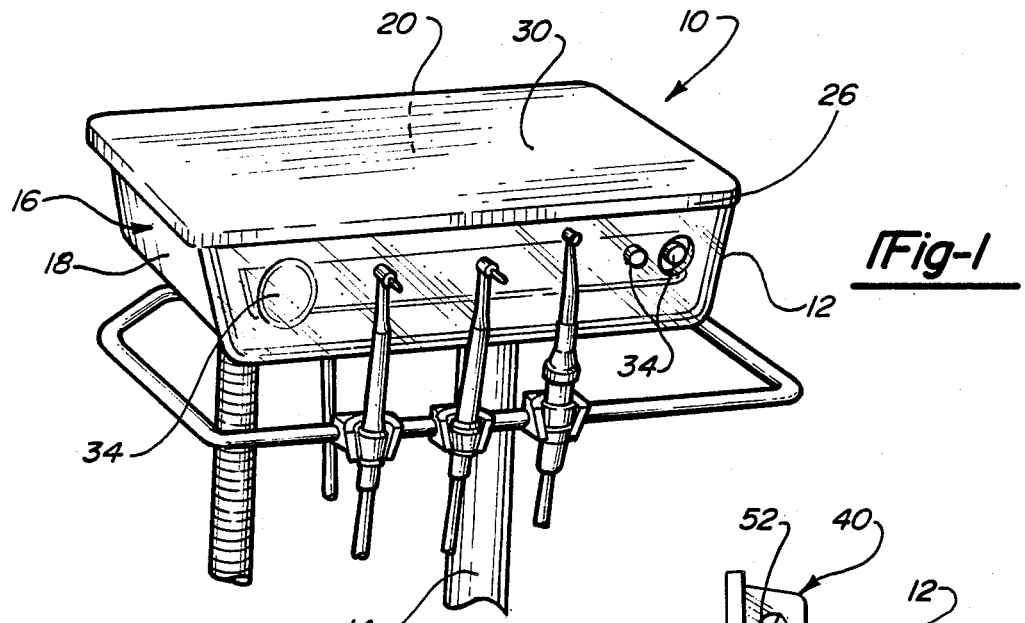
*Fig-1*
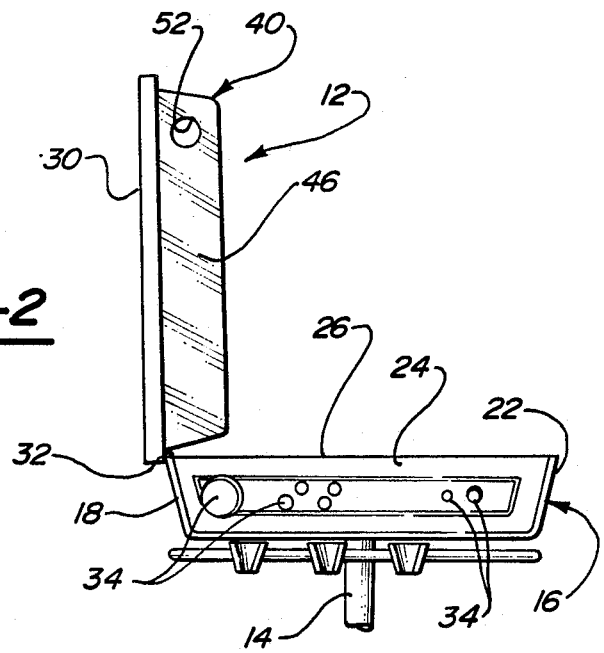
*Fig-2*
*Fig-3*

DENTAL CONTROL UNIT

BACKGROUND OF THE INVENTION

I. Field of the Invention

The present invention relates generally to dentistry and, more particularly, to an improved dental control unit with means to facilitate cleaning and disinfecting after patient use.

II. Description of the Prior Art

Virtually all dentists utilize dental control units, such as dental carts, of one sort or another. These dental carts typically comprise an elevated housing having a plurality of side walls and defining an interior compartment. A lid is pivotally secured to one of the side walls and is movable between an open and a closed position. In its open position, the dentist gains access into the housing compartment. Conversely, when the lid is in its closed position, the lid overlies and covers the open top of the housing.

Additionally, a plurality of gauges, knobs, buttons, outlets, etc., hereinafter collectively referred to as "control members" are provided along one side wall of the dental cart housing. These various control members enable the dentist to set suction pressure, water pressure and the like in order to satisfy the individual preferences of the dentist. Typically, however, once these control members are set by the dentist, further adjustment is rarely, if ever, required.

In the modern day practice of dentistry, it has become increasingly important to disinfect the dental work station after each patient use and, especially, after treatment of a patient with an infectious disease. The disinfection of the dental work station is typically accomplished by wiping a disinfectant on all areas adjacent the dental work station, including the dental cart. The dental cart, however, is especially difficult to disinfect due to the various control members along one side of the cart's side wall. More specifically, in order to completely disinfect the cart, it is necessary to remove the control member knobs and to carefully wipe around all of the crooks and crannies formed by and adjacent the control members. Consequently, this procedure is not only time consuming but also relatively difficult to achieve complete disinfection of the dental cart.

SUMMARY OF THE PRESENT INVENTION

The present invention provides a combination dental cart and shield which overcomes all of the above mentioned disadvantages of the previously known devices.

In brief, the present invention provides a shield assembly for use in combination with a dental cart. The dental cart itself is conventional in construction and comprises a housing having an open top and defining an interior compartment. A lid is pivotally secured to one side wall of the dental cart and movable between an open position in which the interior of the cart is accessible and a closed position in which the lid closes and overlies the open top of the dental cart housing.

Similarly, in the conventional fashion, a plurality of control members are provided along one side wall of the dental cart. These control members typically include gauges, knobs, switches, buttons, fluid ports and the like.

The shield assembly generally comprises an elongated flat panel which is constructed of a transparent material. The flat panel is secured to the lid of the dental cart so that, when the lid is in its closed position, the panel overlies and covers the control members. Furthermore, the panel is constructed of a smooth material which is easily wiped with a disinfectant thereby facilitating disinfection of the dental cart.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 1 is a perspective view illustrating a preferred embodiment of the present invention;

FIG. 2 is a side view of the preferred embodiment but showing the lid of the dental cart in an open position; and FIG. 3 is a fragmentary exploded view showing a preferred embodiment of the invention.

DETAILED DESCRIPTION OF A PREFERRED EMBODIMENT OF THE PRESENT INVENTION

With reference to FIGS. 1 and 2, a preferred embodiment of the present invention is thereshown and comprises a dental cart 10 in combination with a shield assembly 12. Both the dental cart 10 and the shield assembly 12 will be further described in detail.

Still referring to the drawing, the dental cart 10 is conventional in construction and includes a stand 14 (only partially shown) having a housing 16 at its upper end. The housing 16 is generally rectangular in shape and has four side walls 18, 20, 22 and 24 which are secured together in any conventional fashion. The side walls 18–24 are open at their top 26 thereby forming an interior compartment.

A lid 30 is pivotally mounted by a hinge 32 to one side wall 18 of the housing 16. The lid 30 is movable between an open position, illustrated in FIG. 2, and a closed position, illustrated in FIG. 1. In its closed position, the lid 30 overlies and covers the open top 26 of the housing 16 while, conversely, when the lid is in its open position, an interior compartment of the dental cart is accessible.

As best shown in FIGS. 1 and 2, a plurality of dials, knobs, buttons, fluid ports and the like, hereinafter collectively referred to as "control members 34" are provided along one side wall 24 of the housing 16. These control members 34 are typically adjusted only infrequently by the dentist.

Referring now particularly to FIGS. 2 and 3, the shield assembly 12 comprises an elongated panel 40 having two legs 42 and 44 which are generally perpendicular to each other and are secured together along one edge. The panel 40 is constructed of a transparent material, such as plexiglass, lexan, glass or the like. In addition, the outer surface 46 of the panel leg 42 is smooth and easily wipable and, preferably, generally planar for a reason to be subsequently described.

As best shown in FIG. 3, the leg 44 of the panel 40 is secured to a bottom 48 of the lid 30 by conventional fasteners 50, such as screws. Furthermore, the panel 40 is dimensioned and is secured to the lid 30 so that, when the lid 30 is in its closed position, the legs 42 of the panel 40 is generally parallel to, but spaced outwardly from, the housing side wall 24 and thus spaced outwardly from the control members 34. Consequently, the leg 42 of the panel 40 overlies and covers the control members 34 on the dental cart 10.

Even though the panel 40 overlies and covers the control members 34 on the dental cart 10, these controls are still visible through the panel 40 and are also accessible for adjustment by opening the lid 30 to the position shown in FIG. 2.

In some cases, however, it is necessary for the dentist to connect an instrument to one of the control members 34 on the dental cart 30. For this purpose, an opening 52 (FIG. 2) is provided through the panel leg 42 which registers with the control member 34 when the lid is closed. The opening 52 enables the dentist to utilize such an instrument.

In operation, the lid 30 is moved to its closed position (FIG. 1) when the dentist performs dental treatment on the patient. After the dental treatment is completed and the patient discharged, the dental cart can be easily and rapidly disinfected by merely wiping a disinfectant across the top of the lid 30 as well as along the outside surface 42 of the shield 12. Since the shield 12 overlies and covers the various control members 34, it is not necessary for the dentist to individually wipe the various control members 34 as has been the previous practice.

Although the shield assembly has been described for use with a dental cart, it may also be used with other types of dental control units, such as a front delivery system and a rear delivery system. Such front and rear delivery systems include a housing with a side wall having one or more control members. In this event, the shield assembly is preferably pivotally mounted to the housing for the front or rear delivery system to provide access to the control members when required.

From the foregoing, it can be seen that the present invention provides a simple, inexpensive and yet totally effective means to facilitate disinfection of a dental cart following patient treatment.

Having described my invention, however, many modifications thereto will become apparent to those skilled in the art to which it pertains without deviation from the spirit of the invention as defined by the scope of the appended claims.

I claim:

1. In combination a shield assembly and a dental cart, said dental cart having a housing with a plurality of side walls and an open top, a lid, means for pivotally mounting said lid to one of said side walls so that said lid is movable between an open position and a closed position, wherein in said closed position said lid overlies and covers the open top of said housing while in said open position said lid uncovers the open top of said housing and enables access into the interior of the housing, said housing having at least one control member on one of said side walls, said shield assembly comprising:

a panel, said panel being constructed of a transparent material, means securing said panel to said lid so that, when said lid is in said closed position, said panel overlies and covers said at least one control member and wherein said panel is dimensioned so that, when said lid is in said open position, said panel is spaced from said control member to thereby provide access to said control member, wherein said panel has a smooth and easily wipable outer surface.

2. The invention as defined in claim 1 wherein said panel comprises two legs which are joined together along an edge and are generally perpendicular to each other, a first of said legs being secured to said lid.

3. The invention as defined in claim 2 wherein a second leg of said panel lies substantially in a vertical plane.

4. The invention as defined in claim 3 wherein said other leg of said panel is spaced from and substantially parallel from said one side of said housing.

5. The invention as defined in claim 2 wherein said securing means comprises means securing said first leg to a bottom of said lid.

6. The invention as defined in claim 1 wherein said panel is made of plexiglass.

7. The invention as defined in claim 1 wherein said panel includes an opening which registers with the control member when the lid is closed.

* * * * *